United States Patent
Lee et al.

(10) Patent No.: US 8,486,670 B2
(45) Date of Patent: Jul. 16, 2013

(54) **METHOD OF PRODUCING L-THREONINE USING *ESCHERICHIA COLI* STRAIN WITH PHOSPHOENOLPYRUVATE CARBOXYLASE PROMOTER REPLACED WITH CYSTEINE SYNTHASE PROMOTER**

(71) Applicants: Kwang Ho Lee, Daejeon (KR); Jae Yeong Ju, Seongnam-si (KR); Ji Sun Lee, Incheon (KR); Young Bin Hwang, Seoul (KR); Sung Hoo Jhon, Seoul (KR); Eun Sung Koh, Suwon-si (KR); Chul Ha Kim, Seoul (KR); Soo An Shin, Seoul (KR)

(72) Inventors: Kwang Ho Lee, Daejeon (KR); Jae Yeong Ju, Seongnam-si (KR); Ji Sun Lee, Incheon (KR); Young Bin Hwang, Seoul (KR); Sung Hoo Jhon, Seoul (KR); Eun Sung Koh, Suwon-si (KR); Chul Ha Kim, Seoul (KR); Soo An Shin, Seoul (KR)

(73) Assignee: Cheiljedang Corp. (KR)

( * ) Notice: Subject to any disclaimer, the term of this patent is extended or adjusted under 35 U.S.C. 154(b) by 0 days.

(21) Appl. No.: 13/658,369

(22) Filed: Oct. 23, 2012

(65) Prior Publication Data
US 2013/0040347 A1    Feb. 14, 2013

Related U.S. Application Data

(62) Division of application No. 12/812,203, filed as application No. PCT/KR2009/000066 on Jan. 7, 2009.

(30) Foreign Application Priority Data

Jan. 8, 2008 (KR) .................. 10-2008-0002310

(51) Int. Cl.
*C12P 13/08* (2006.01)

(52) U.S. Cl.
USPC ........................................... 435/115

(58) Field of Classification Search
None
See application file for complete search history.

(56) References Cited

U.S. PATENT DOCUMENTS

| | | | |
|---|---|---|---|
| 5,538,873 | A | 7/1996 | Debabov et al. |
| 5,939,307 | A | 8/1999 | Wang et al. |
| 7,229,794 | B2 | 6/2007 | Park et al. |
| 2005/0124049 | A1 | 6/2005 | Ziyatdinov et al. |
| 2006/0205044 | A1 | 9/2006 | D'Elia et al. |

FOREIGN PATENT DOCUMENTS

| | | |
|---|---|---|
| JP | 1993-227977 A | 9/1993 |
| KR | 1992-0008365 A | 9/1992 |
| KR | 10-0478468 A | 3/2005 |
| WO | 02/31172 A2 | 4/2002 |
| WO | 2004/087937 A1 | 10/2004 |
| WO | 2006/062327 A1 | 6/2006 |
| WO | 2006065095 A1 | 6/2006 |
| WO | WO 2008/127240 A1 * | 10/2008 |

OTHER PUBLICATIONS

Chao, Y.P. et al., Alteration of growth yield by overexpression of phosphoenolpyruvate carboxylase and phosphoenolpyruvate carboxykinase in *Escherichia coli*, Appl Environ Microbiol. Dec. 1993;59(12):4261-4265.
International Search Report and Written Opinion (in Korean) issued Jun. 2, 2009 for PCT/KR2009/000066; citing US 5,939,307, US 2006/0205044, KR 10-0478468 and WO 2002/031172.
Arakawa, H et al., "Mutant loxP vectors for selectable marker recycle and conditional knock-outs", BMC Biotechnology, 2001, vol. 1:7; 8 pages.
Wanner, B.L. et al.,"One-step inactivation of chromosomal genes in *Escherichia coli* K-12 using PCR products", Proc Natl Acad Sci USA, 2000, 97(12): 6640-6645.
Nagy, A., "Cre Recombinase: The Universal Reagent for Genome Tailoring", Genesis., 2000, vol. 26., 99-109.
Suzuki, N. et al., "New Multiple-Deletion Method of the *Corynebacterium glutamicum* Genome, Using a Mutant lox Sequence" Applied and Environmental Microbiology, 2005, vol. 71:12; 8472-8480.
Sambrook, J. et al., "Molecular Cloning", Cold Spring Harbor Laboratory Press; 2nd edition, 1989, pp. 1.30-1.59.
Sambrook, J. et al., "Molecular Cloning", Cold Spring Harbor Laboratory Press; 2nd edition, 1989, pp. 1.50-1.110.
Ishida, M. et al., "Improvement of an L-Threonine Producer Derived from *Brevibacterium flavum* Using Threonine Operon of *Escherichia coli* K-12", Agric. Biol. Chem., 1989, vol. 53:8.; 2269-2271.
Lee, K.H. et al., Systems metabolic engineering of *Escherichia coli* for L-threonine production, Mol Syst Biol. 2007; 3(149): 1-8.
European Extended Search Report for Application No. 09700769.4 dated Jan. 28, 2011.
Colyer, T. E. et al., In vitro characterization of constitutive CysB proteins from *Salmonella typhimurium*, Mol Microbiol. 1996; 21(2): 247-256.
Fang, F. et al, Characterization of endogenous plasmids from *Lactobacillus salivarius* UCC118, Appl Environ Microbiol. 2008; 74(10): 3216-3128.
Alper, H. et al., Tuning genetic control through promoter engineering, Proc Natl Acad Sci U S A. 2005; 102(36): 12678-12683. (Correction published Proc Natl Acad Sci U S A. 2006; 03(8): 3006-3007).
Brosius, J. et al., Spacing of the -10 and -35 regions in the tac promoter. Effect on its in vivo activity, J Biol Chem. 1985; 260(6): 3539-3541. Abstract Only.

* cited by examiner

*Primary Examiner* — David J Steadman
(74) *Attorney, Agent, or Firm* — Cantor Colburn LLP

(57) ABSTRACT

An L-threonine-producing *Escherichia coli* in which a promoter of a phosphoenolpyruvate carboxylase (ppc) gene on the chromosome is substituted with a promoter of a cysteine synthase (cysK) gene and a method of producing L-threonine by using the same are disclosed. The recombinant *Escherichia coli* may produce L-threonine in a high yield, and thus may be widely used in medical, pharmaceutical, and feed industries, particularly for an animal feed.

2 Claims, 2 Drawing Sheets

Figure 1:
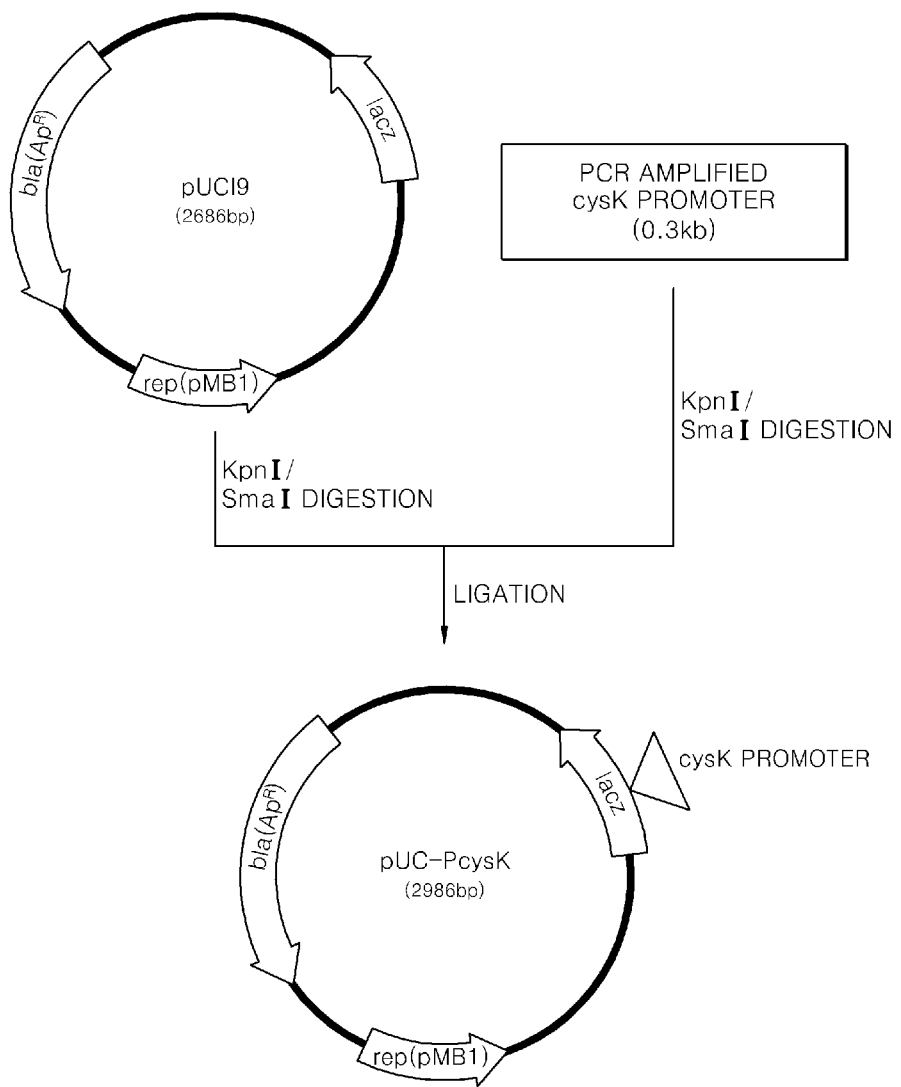

METHOD OF PRODUCING L-THREONINE USING ESCHERICHIA COLI STRAIN WITH PHOSPHOENOLPYRUVATE CARBOXYLASE PROMOTER REPLACED WITH CYSTEINE SYNTHASE PROMOTER

This application is a division of U.S. patent application Ser. No. 12/812,203, which is the United States national stage application of PCT/KR09/000,066, filed Jan. 7, 2009, which claims priority to Korean Patent Application No. 10-2008-0002310, filed Jan. 8, 2008, under provisions of 35 U.S.C. 119 and the International Convention for the protection of Industrial Property, the disclosures of each are incorporated by reference in their entirety.

TECHNICAL FIELD

One or more embodiments of the present invention relate to an L-threonine-producing *Escherichia coli* (*E. coli*) strain with enhanced L-threonine productivity in which a promoter of a phosphoenolpyruvate carboxylase (ppc) gene on the chromosome is substituted with a promoter of a cysteine synthase (cysK) gene, and a method of producing L-threonine using the same.

BACKGROUND ART

L-threonine is an essential amino acid and is widely used as an animal feed additive or food additive, and is also used as a raw material for medical fluid or drug synthesis. While animal protein contains a sufficient amount of L-threonine, vegetable protein is deficient in L-threonine. Thus, L-threonine is likely to be deficient in animals mainly on vegetarian diets, and thus in particular it is widely used as an additive for animal feed.

L-threonine is produced mainly by a fermentation process using *Escherichia coli* (*E. coli*) or *Corynebacterium*, which is developed by artificial mutagenesis or genetic recombination. To produce L-threonine, a mutant strain derived from a wild-type strain of *Escherichia coli* (*E. coli*), *Corynebacteria* sp., *Serratia* sp., or *Providencia* sp is used. Examples of the mutant strain include an amino acid analogue- or drug-resistant mutant strain, and a diaminopimellic acid, a methionine, a lysine, or an isoleucine auxotrophic mutant strain that has also an amino acid analogue- or drug-resistance. Among methods of producing L-threonine using a mutant strain, a method of using a microorganism that belongs to *Escherichia coli* species, has diaminopimellic acid and methionine auxotroph phenotypes, and is mutated so that biosynthesis of L-threonine is not affected by feedback inhibition of threonine is disclosed in Japanese Patent No. 10037/81.

A fermentation process using a recombinant strain can also be used in production of L-threonine. For example, Japanese Patent Application Publication No. 05-227977 discloses a method of producing L-threonine using a recombinant *E. coli* into which a threonine operon consisting of genes encoding aspartokinase, homoserine dehydrogenase, homoserine kinase, and threonine synthase is introduced in a plasmid form, and a method of producing L-threonine using threonine-producing *Brevibacterium flavum* into which a threonine operon derived from *E. coli* is introduced (TURBA E, et al, *Agric. Biol. Chem.* 53:2269~2271, 1989).

In general, the expression of a specific gene in a microorganism may be enhanced by increasing the copy number of the gene in the microorganism. For this, a plasmid that gives a greater copy number to a microorganism is used [Sambrook et al., *Molecular Cloning*, 2th, 1989, 1.3-1.5]. That is, the number of the gene may be increased by as many as the copy number of the plasmid per a single microorganism by inserting a target gene into the plasmid whose copy number may be maintained at a high level and then transforming the microorganism with the obtained recombinant plasmid. Attempts have also been made to enhance the productivity of threonine using this method and a partial success was reported (U.S. Pat. No. 5,538,873). However, this technology using a plasmid induces excessive expression of only a specific gene in most cases, thereby imposing a heavy burden on a host microorganism. Furthermore, plasmids may be lost during culturing of a recombinant strain, thereby decreasing plasmid stability. To address these problems of the method of producing threonine by using a recombinant strain into which a plasmid is introduced, addition of an antibiotic into a culture and methods of using a plasmid whose expression is controllable have been developed [Sambrook et al. *Molecular Cloning*, 2th, 1989, 1.5-1.6, 1.9-1.11]. In the case of using the plasmid whose expression is controllable, to alleviate the burden on a host microorganism and obtain a large amount of cells, during the growth phase, a host microorganism is cultured under conditions where the expression of a target gene on the plasmid does not occur, and after the sufficient growth of the host microorganism, temporary expression of the gene is induced, thereby obtaining a target material. However, methods using plasmids whose expression is controllable can be used only when a final gene product is a protein or a secondary metabolite. In a case where a gene product is a primary metabolite that is produced at the same time when microorganisms begin to grow, expression of a target gene must be induced during the growth phase. Otherwise, it is difficult to anticipate the accumulation of the primary metabolite. Since threonine belongs to a primary metabolite, the latter case is also applied to threonine.

Thus, to enhance the productivity of threonine, which is a primary metabolite, inserting genes involved in threonine biosynthesis into chromosomal DNA of a microorganism is disclosed in U.S. Pat. No. 5,939,307, instead of using a method of introducing a plasmid with threonine biosynthesis-related genes into a microorganism. Methods of increasing the threonine biosynthesis-related genes and the expression thereof have been diversely developed, but there is still a need for developing a method of more economically producing L-threonine in a high yield.

To increase the production yield of L-threonine, research on a biosynthesis pathway from oxaloacetate to threonine has been intensively conducted. With regards to this, we intended to first induce the flow of carbon along a pathway from phosphoenolpyruvate to oxaloacetate by enhancing the activity of phosphoenolpyruvate carboxylase involved in a step right before the biosynthesis of L-threonine. For this, we studied and found that a microorganism strain capable of producing L-threonine in which a promoter of a phosphoenolpyruvate carboxylase (ppc) gene on the chromosome was substituted with a promoter of a gene encoding cysteine synthase (cysK) so as to increase the expression of a gene encoding ppc, which is a first enzyme in the biosynthesis of L-threonine after glycolysis, produced L-threonine in a high yield, thus completing the present invention.

DISCLOSURE OF INVENTION

Technical Problem

One or more embodiments of the present invention provide an *Escherichia coli* (*E. coli*) strain capable of producing L-threonine in high yield.

One or more embodiments of the present invention also provide a method of producing L-threonine using the *E. coli* strain, whereby L-threonine may be efficiently produced.

Technical Solution

The present invention provides an L-threonine-producing microorganism in which a promoter of a natural phosphoenolpyruvate carboxylase (ppc) gene on the chromosome is substituted with a promoter of cysteine synthase (cysK) gene.

In the L-threonine-producing microorganism, the expression of ppc increases in such a way that a promoter of a gene encoding ppc, which converts phosphoenolpyruvate produced after glycolysis to oxaloacetate, the starting material of L-threonine biosynthesis, is substituted with the promoter of the cysK gene, and the productivity of L-threonine may increase, accordingly.

The microorganism may include a prokaryotic or eukaryotic cell capable of producing L-threonine in which a promoter of a ppc gene on the chromosome is substituted with a promoter of a cysK gene. For example, the microorganism may be a microorganism strain belonging to *Escherichia* genus, *Erwinia* genus, *Serratia* genus, *Providencia* genus, *Corynebacterium* genus, or *Brevibacterium* genus. In particular, the microorganism may be a microorganism belonging to Enterobacteriaceae family, and more particularly, a microorganism belonging to *Escherichia* genus. Most particularly, the microorganism may be *Escherichia coli* CA030031 (KCCM 10910P).

The *E. coli* CA030031 is derived from *E. coli* KCCM 10541 which is derived from a L-threonine-producing *E. coli*, KFCC 10718 (Korean Patent Publication No. 92-8395). The *E. coli* KFCC 10718 has a resistance to an L-methionine analogue, a methionine auxotroph phenotype, a resistance to an L-threonine analogue, a leaky isoleucine auxotroph phenotype, a resistance to an L-lysine analogue, and a resistance to α-aminobutyric acid, and is capable of producing L-threonine. Thus, the microorganism may also include a mutant microorganism for producing L-threonine, in addition to a wild-type microorganism. For example, the mutant microorganism may be a microorganism that has a resistance to an L-methionine analogue, a methionine auxotroph phenotype, a resistance to an L-threonine analogue, a leaky isoleucine auxotroph phenotype, a resistance to an L-lysine analogue, and a resistance to α-aminobutyric acid, and belongs to *E. coli* capable of producing L-threonine.

In an embodiment, the microorganism may be *E. coli* that has a methionine auxotroph phenotype and resistances to a threonine analogue, a lysine analogue, an isoleucine analogue and a methionine analogue. For example, the L-methionine analogue may be at least one compound selected from the group consisting of D,L-methionine, norleucine, α-methyl-methionine, and L-methionine-D,L-sulfoximine, the L-threonine analogue may include at least one compound selected from the group consisting of α-amino-β-hydroxy valeric acid and D,L-threonine hydroxamate, and the L-lysine analogue may be at least one compound selected from the group consisting S-(2-aminoethyl)-L-cysteine and δ-methyl-L-lysine. Examples of the mutant microorganism may include a microorganism in which a pckA gene involved in converting oxaloacetate (OAA) into phosphoenol pyruvate (PEP), which is an intermediate involved in the biosynthesis of L-threonine, is inactivated, a microorganism in which a tyrR gene repressing a lysC gene which is involved in conversion of oxaloacetate into aspartate is inactivated, or a microorganism in which a galR gene repressing the expression of a galP gene which is involved in the influx of glucose is inactivated.

In the microorganism of the present invention, the promoter of the ppc gene on the chromosome is substituted with the promoter of the cysK gene so as to increase the expression thereof. The promoter of the cysK gene used herein may be derived from a cysK gene with a high expression rate, and may have a nucleotide sequence of SEQ ID NO: 10.

The present invention also provides a method of producing L-threonine, the method including: culturing a transformed microorganism with enhanced L-threonine productivity in which a promoter of a natural ppc gene on the chromosome is substituted with a promoter of a cysK gene; and isolating L-threonine from the culture of the microorganism.

In the method of producing L-threonine, the transformed microorganism may be *E. coli*, for example, *E. coli* CA030031 (KCCM 10910P).

One or more embodiments of the present invention will now be described more fully with reference to the following examples. However, these examples are provided only for illustrative purposes and are not intended to limit the scope of the present invention.

Advantageous Effects

As described above, according to the present invention, in a microorganism in which a promoter of a ppc gene on the chromosome is substituted with a promoter of a cysK gene, the expression of the ppc gene, which is an enzyme converting phosphoenolpyruvate to oxaloacetate that is a precursor of L-threonine biosynthesis, increases, thereby significantly enhancing the productivity of L-threonine by 16% or higher. The microorganism may produce L-threonine in a high yield, and thus may be widely used in medical, pharmaceutical, and feed industries, particularly for an animal feed.

DESCRIPTIONS OF DRAWINGS

Figure 2:
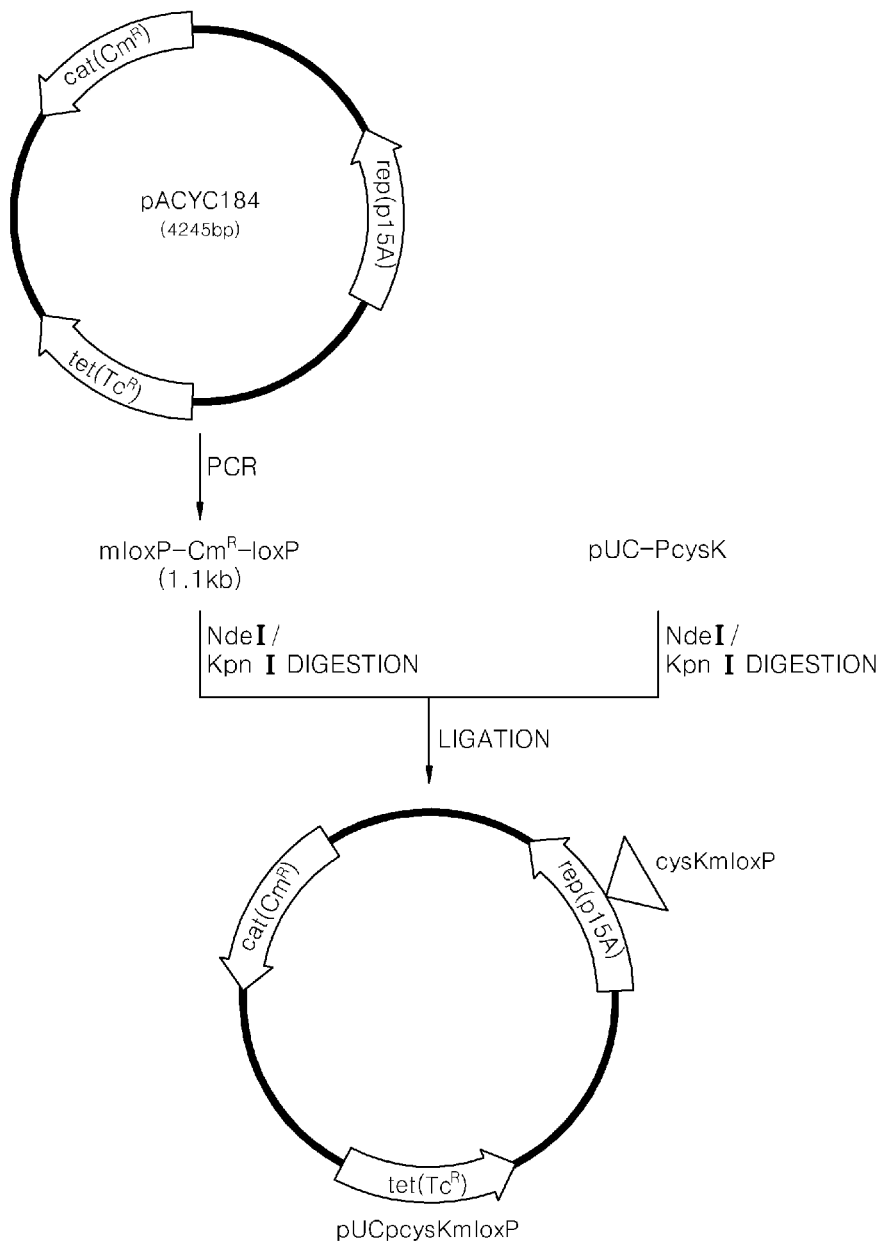

FIG. 1 is a diagram illustrating a process of constructing a recombinant vector pUC-PcysK; and FIG. 2 is a diagram illustrating a process of constructing a recombinant vector pUCpcysKmloxP.

MADE FOR INVENTION

Example 1

Construction of Recombinant Vector pUCpcysKmloxP

Preparation of Pcysk Fragment

To obtain 0.3 kb DNA fragment containing a promoter of a cysK gene (SEQ ID NO: 10), the genomic DNA (gDNA) of W3110, which is *E. coli* wild type strain, was extracted using a QIAGEN Genomic-tip system, and a polymerase chain reaction (PCR) was performed using the gDNA as a template and a PCR HL premix kit (manufactured by BIONEER, Korea). To amplify the promoter of the cysK gene, the PCR was performed using primers of SEQ ID NOS: 1 and 2 as follows: 30 cycles of denaturation at 94° C. for 30 seconds, annealing at 55° C. for 30 seconds and elongation at 72° C. for 2.5 minutes.

The PCR products were digested with KpnI and EcoRV, electrophoresized on a 0.8% agarose gel, and then eluted to obtain 0.3 Kb DNA fragment (hereinafter, referred to as "PcysK fragment").

(2) Construction of Recombinant Vector pUC-PcysK

FIG. 1 is a diagram illustrating a process of constructing recombinant vector pUC-PcysK containing a promoter of a cysK gene.

Plasmid pUC19 (New England Biolabs, USA) and the PcysK fragment obtained according to Example 1-(1) were each digested with restriction enzymes KpnI and SmaI, and ligated with each other to construct vector pUC-PcysK.

(3) Construction of Recombinant Vector pUCpcysKmloxP

FIG. 2 is a diagram illustrating a process of constructing a recombinant vector pUCpcysKmloxP.

In general, in an experiment of gene deletion caused by one-step inactivation, whenever one gene is deleted, one sequence of a recombinase recognition site loxP remains on a chromosomal DNA. It has been reported that due to the sequences of loxP remaining on the chromosomal DNA, when the strains are additionally modified for further development, the efficiency may be significantly decreased (Nagy A., Genesis, 26:99, 2000). An improved method of gene deletion using loxP mutants, which are named lox71 and lox 66 has been proposed by Suzuki (Appl. Environ. Microbiol. 71:8472, 2005). Thus, to more efficiently substitute a promoter of a ppc gene on the chromosome with a promoter of a cysK gene by using the loxP mutants, we constructed vector pUCpcysKmloxP having both a mutant loxP-$Cm^R$-loxP cassette and the promoter of the cysK gene.

As shown in FIG. 2, the PCR was performed using plasmid pACYC184 (New England Biolab) as a template by using primers of SEQ ID NOS: 3 and 4 as follows: 30 cycles of denaturation at 94° C. for 30 seconds, annealing at 55° C. for 30 seconds and elongation at 72° C. for 1 minute to obtain 1.1 kb of PCR fragment. The vector pUC-PcysK constructed according to Example 1-(2) and 1.1 kb of DNA fragment obtained using pACYA184 as a template were each digested with restriction enzymes NdeI/KpnI, ligated with each other, and transformed into E. coli. Then, cell having DNA accurately ligated with the vector were selected using a general method, and plasmid pUCpcysKmloxP was purified from the culture of the cells.

Example 2

Preparation of Recombinant E. coli KCCM 10541-PcyK-ppc

To substitute a native promoter of a ppc gene (SEQ ID NO: 9) encoding phosphoenolpyruvate carboxylase on the chromosome with a promoter of a cysK gene, a known one-step inactivation method (Warner et al., PNAS, 6; 97(12):6640, 2000) was performed on E. coli KCCM 10541.

First, PCR was performed using the plasmid pUCpcysK-mloxP constructed according to Example 1 as a template by using primers of SEQ ID NOS: 5 and 8 as follows: 30 cycles of denaturation at 94° C. for 30 seconds, annealing at 55° C. for 30 seconds and elongation at 72° C. for 1 minute to obtain DNA fragments and the obtained DNA fragments were purified using a QIAGEN kit (PCR Purification kit). Subsequently, PCR was further performed using primers of SEQ ID NOS: 6 and 7 and the purified DNA fragments as a template as follows: 30 cycles of denaturation at 94° C. for 30 seconds, annealing at 55° C. for 30 seconds and elongation at 72° C. for 1 minute. The resulting DNA fragments were purified, the purified DNA fragments were introduced by electroporation into E. coli KCCM 10541 into which vector pKD46 was introduced (Proc. Natl. Acad. Sci. U.S.A. 97(12), 6640-6645 (2000)), and a single colony was selected on a Luria-Bertani (LB) plate containing 15 μg/mL of chloramphenicol. The selected strain was a strain in which the DNA fragment was inserted into a promoter site of a ppc gene. Vector pJW168 (BMG Biothechnol. 2001; 1:7. Epub 2001 Sep. 26) was introduced into the selected strain to prepare recombinant E. coli KCCM 10541-PcyK-ppc in which the naive promoter of the ppc gene was substituted with the promoter of the cysK gene, by removing antibiotics-resistance gene.

Example 3

Comparison in L-Threonine Productivity Between Recombinant Microorganisms

The recombinant microorganism prepared according to Example 2 was cultured in a threonine titer medium, as shown in Table 1 below, in an Erlenmeyer flask, and it was confirmed whether the productivity of L-threonine was improved.

TABLE 1

| Composition | Concentration (per liter) |
|---|---|
| Glucose | 70 g |
| $KH_2PO_4$ | 2 g |
| $(NH_4)_2SO_4$ | 25 g |
| $MgSO_4 \cdot 7H_2O$ | 1 g |
| $FeSO_4 \cdot 7H_2O$ | 5 mg |
| $MnSO_4 \cdot 4H_2O$ | 5 mg |
| DL-methionine | 0.15 g |
| Yeast extract | 2 g |
| Calcium carbonate | 30 g |
| pH | 6.8 |

1 platinum loop of E. coli KCCM 10541 and E. coli KCCM 10541-PcysK-ppc that were cultured in a LB solid medium in an incubator at 33° C. overnight were each inoculated in 25 ml of titer medium, as shown in Table 1, and cultured in the incubator at 33° C. at 200 rpm for 48 hours. The results are shown in Table 2 below.

As shown in Table 2, when the parent strain E. coli KCCM 10541 was cultured for 48 hours, it produced 29.8 g/L of L-threonine, while the E. coli KCCM 10541-PcysK-ppc of Example 2 produced 34.7 g/L of L-threonine, which has a 4.9 g/L higher productivity than that of the parent strain. Thus, it was confirmed that the recombinant strain in which the promoter of the ppc gene was substituted with the promoter of the cysK gene has enhanced L-threonine productivity. The transformed E. coli KCCM 10541-PcysK-ppc was named E. coli CA030031 and deposited in Korean Culture Center of Microorganisms (KCCM) on Dec. 20, 2007 (Accession No: KCCM 10910P).

TABLE 2

| Strain | L-threonine (g/L) |
|---|---|
| KCCM10541 (parent strain) | 29.8 |
| KCCM10541-PcysK-ppc | 34.7 |

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing L-threonine, the method comprising:
   culturing an *Escherichia coli* strain to produce L-threonine and
   isolating L-threonine from the culture of the *Escherichia coli* strain,
   wherein the *Escherichia coli* strain is modified by substituting a promoter of a phosphoenolpyruvate carboxylase (ppc) gene on the chromosome of said *Escherichia coli* strain with a promoter of a cysteine synthase (cysK) gene,
   wherein the promoter of the cysK gene has the nucleotide sequence of SEQ ID No:10, and wherein the expression of the ppc gene in the modified *Escherichia coli* strain is increased relative to an *Escherichia coli* strain without said substitution.

2. The method of producing L-threonine according to claim 1, wherein the *Escherichia coli* strain is the *Escherichia coli* stain having Korean Culture Center of Microorganism Accession No: KCCM 10910P).

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: primer for cysK promoter

<400> SEQUENCE: 1
cagaggtacc ccagcctgtt tacgatgatc         30

<210> SEQ ID NO 2
<211> LENGTH: 30
<212> TYPE: DNA
<213> ORGANISM: Artificial Sequence
<220> FEATURE:
<223> OTHER INFORMATION: primer for cysK promoter

<400> SEQUENCE: 2
gactgatatc gtgaccgata gtcagcgagt         30

<210> SEQ ID NO 3
<211> LENGTH: 64
<212> TYPE: DNA
<213> ORGANISM: Artificial Sequence
<220> FEATURE:
<223> OTHER INFORMATION: primer

<400> SEQUENCE: 3
atatcatatg taccgttcgt atagcataca ttatacgaag ttatctgccc tgaaccgacg         60
accg         64

<210> SEQ ID NO 4
<211> LENGTH: 65
<212> TYPE: DNA
<213> ORGANISM: Artificial Sequence
<220> FEATURE:
<223> OTHER INFORMATION: primer

<400> SEQUENCE: 4
aattccatgg taccgttcgt ataatgtatg ctatacgaag ttatgcatca cccgacgcac         60
tttgc         65

<210> SEQ ID NO 5
<211> LENGTH: 70
<212> TYPE: DNA
<213> ORGANISM: Artificial Sequence
<220> FEATURE:
<223> OTHER INFORMATION: primer

<400> SEQUENCE: 5
cttgcgcatc ttatccgacc tacacctttg gtgttacttg ggcgattttt aaggcgatta         60
agttgggtaa         70

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6

```
atccggcact gttgccaaac tccagtgccg caataatgtc ggatgcgata cttgcgcatc    60
ttatccgacc                                                          70

<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
ttgccgagca tactgacatt actacgcaat gcggaatatt gttcgttcat gatatctcct    60
taactgtatg                                                          70

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
gttcaagaat gtgttctccc aacgcatcct tgatggtttc tcccagcact ttgccgagca    60
tactgacatt                                                          70

<210> SEQ ID NO 9
<211> LENGTH: 2652
<212> TYPE: DNA
<213> ORGANISM: Escherichia coli

<400> SEQUENCE: 9
atgaacgaac aatattccgc attgcgtagt aatgtcagta tgctcggcaa agtgctggga    60
gaaaccatca aggatgcgtt gggagaaacac attcttgaac gcgtagaaac tatccgtaag   120
ttgtcgaaat cttcacgcgc tggcaatgat gctaaccgcc aggagttgct caccaccta   180 caaaatttgt cgaacgacga gctgctgccc gttgcgcgtg cgtttagtca gttcctgaac   240
ctggccaaca ccgccgagca ataccacagc atttcgccga aggcgaagc tgccagcaac   300 ccggaagtga tcgcccgcac cctgcgtaaa ctgaaaaacc agccggaact gagcgaagac   360
accatcaaaa aagcagtgga tcgctgtcg ctggaactgg tcctcacggc tcacccaacc   420
gaaattaccc gtcgtacact gatccacaaa atggtggaag tgaacgcctg tttaaaacag   480
ctcgataaca aagatatcgc tgactacgaa cacaaccagc tgatgcgtcg cctgcgccag   540
ttgatcgccc agtcatggca taccgatgaa atccgtaagc tgcgtccaag cccggtagat   600
gaagccaaat ggggctttgc cgtagtgaa acagcctgt ggcaaggcgt accaaattac    660
ctgcgcgaac tgaacgaaca actggaagag aacctcggct acaaactgcc cgtcgaattt   720
gttccggtcc gttttacttc gtggatgggc ggcaccgcg acggcaaccc gaacgtcact   780
gccgatatca cccgccacgt cctgctactc agccgctgga agccaccga tttgttcctg   840 aaagatattc aggtgctggt ttctgaactg tcgatggttg aagcgacccc tgaactgctg   900
gcgctggttg gcgaagaagg tgccgcagaa ccgtatcgct atctgatgaa aaacctgcgt   960
tctcgcctga tggcgacaca ggcatggctg aagcgcgcc tgaaaggcga agaactgcca  1020
aaaccagaag gcctgctgac acaaaacgaa gaactgtggg aaccgctcta cgcttgctac  1080
cagtcacttc aggcgtgtgg catgggtatt atcgccaacg gcgatctgct cgacaccctg  1140
cgccgcgtga atgtttcgg cgtaccgctg gtccgtattg atatccgtca ggagagcacg  1200
```

-continued

```
cgtcataccg aagcgctggg cgagctgacc cgctacctcg gtatcggcga ctacgaaagc    1260
tggtcagagg ccgacaaaca ggcgttcctg atccgcgaac tgaactccaa acgtccgctt    1320
ctgccgcgca actggcaacc aagcgccgaa acgcgcgaag tgctcgatac ctgccaggtg    1380
attgccgaag caccgcaagg ctccattgcc gcctacgtga tctcgatggc gaaaacgccg    1440
tccgacgtac tggctgtcca cctgctgctg aaagaagcgg gtatcgggtt tgcgatgccg    1500
gttgctccgc tgtttgaaac cctcgatgat ctgaacaacg ccaacgatgt catgacccag    1560
ctgctcaata ttgactggta tcgtggcctg attcagggca acagatggt gatgattggc     1620 tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc cagaaatcac cgtcagcagc ctgtcgcttt ataccggggc gattctggaa    1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaaagaagg ccaggaaccg    2580
gatcctcgcg tcgaacaagc gttaatggtc actattgccg ggattgcggc aggtatgcgt    2640
aataccggct aa                                                        2652

<210> SEQ ID NO 10
<211> LENGTH: 148
<212> TYPE: DNA
<213> ORGANISM: Escherichia coli

<400> SEQUENCE: 10
ggcctgtcct taactgtatg aaattgggat acaacaggta gcatacccgc cagagaatat      60
gcggaagtaa ggatttagca tatctatata cagaagggaa ataatgacag caagatggaa    120
taaggggcgg cataagccac ccctgttt                                        148
```